US00PP18228P2

(12) United States Plant Patent
Dean

(10) Patent No.: US PP18,228 P2
(45) Date of Patent: Nov. 20, 2007

(54) ***LIBERTIA* PLANT NAME 'NNGF2'**

(50) Latin Name: *Libertia*
Varietal Denomination: NNGF2

(76) Inventor: Mark Dean, 30 Gammon Mill Road, Oropi, RD3, Tauranga (NZ)

( * ) Notice: Subject to any disclaimer, the term of this patent is extended or adjusted under 35 U.S.C. 154(b) by 51 days.

(21) Appl. No.: 11/442,434

(22) Filed: May 26, 2006

(51) Int. Cl.
*A01H 5/00* (2006.01)

(52) U.S. Cl. ..... Plt./384

(58) Field of Classification Search ..... Plt./384
See application file for complete search history.

*Primary Examiner*—Kent Bell
*Assistant Examiner*—Annette H Para

(57) ABSTRACT

A new cultivar of *Libertia* named 'NNGF2' that is characterized by compact fan-shaped clumping habit, golden-yellow foliage, and white star-like flowers. In combination these traits set 'NNGF2' apart from all other existing varieties of *Libertia* known to the inventor.

2 Drawing Sheets

Genus: *Libertia*. Species: *ixioides*.
Denomination: 'NNGF2'.

BACKGROUND OF THE INVENTION

The present invention relates to a new and distinct cultivar of New Zealand iris grown for use as an ornamental plant for container, border, deck, and patio. The new cultivar is known botanically as *Libertia ixioides* and will hereinafter be referred to by the cultivar name 'NNGF2'.

'NNGF2' was discovered by the inventor at the inventor's nursery in Whenuapai, Auckland, New Zealand in 2002. The new *Libertia* variety 'NNGF2' was discovered as a naturally occurring seedling selection within a commercially grown crop of *Libertia* 'Goldfinger' (unpatented). Selection was based on the criterion of gold-yellow foliage. The female parent is an individual *Libertia ixioides* 'Goldfinger' and the male parent is an individual *Libertia ixioides* 'Goldfinger'. The closest comparison plant known to the inventor is a *Libertia ixioides* 'Goldfinger' which exhibits foliage that is orange-yellow in color. 'NNGF2' is distinguishable from the comparison plant by a prominent golden-yellow central stripe on the leaf.

'NNGF2' is distinguishable from all other *Libertia* known to the inventor, by bright golden-yellow foliage, and profusions of white star-like flowers from mid-spring. In fall, flowers give way to large yellow berries. Asexual propagation is accomplished by the methods of tissue culture and division. Cultural requirements are moist, fertile soil, full sun to light shade and adequate but not excess water. Mature height and breadth is 0.60 m. 'NNGF2' is hardy to USDA Zone 7.

'NNGF2' was first asexually propagated in 2004 in Auckland, New Zealand. Asexual propagation was conducted by the inventor using the method of tissue culture. Since that time under careful observation 'NNGF2' has been determined stable, uniform, and reproduces true to type in successive generations of asexual propagation.

SUMMARY OF THE INVENTION

The following traits have been repeatedly observed and represent the distinguishing characteristics of the new *Libertia* variety known as 'NNGF2'. These traits in combination distinguish 'NNGF2' from all other varieties of *Libertia* known to the inventor. 'NNGF2' has not been tested under all possible conditions and phenotypic differences may be observed with variations in environmental, climatic, and cultural conditions, however, without any variance in genotype. Growing requirements are similar to the species.

1. 'NNGF2' exhibits compact clumping habit.
2. 'NNGF2' exhibits bright golden-yellow foliage.
3. 'NNGF2' exhibits fan-shaped habit.
4. 'NNGF2' is grown as an ornamental plant for container, border, deck, and patio.
5. 'NNGF2' exhibits profusions of white star-like flowers from mid-spring to summer.
6. Following the flowers 'NNGF2' exhibits large yellow berries in fall.
7. 'NNGF2' is propagated by the methods of tissue culture and division.
8. At maturity 'NNGF2' reaches 0.60 m. in height and breadth.
9. 'NNGF2' is hardy to USDA Zone 7.
10. Cultural requirements for 'NNGF2' include adequate but not excess water, moist fertile soil, and full sun to light shade.

BRIEF DESCRIPTION OF THE DRAWINGS

The accompanying color drawings illustrate the overall appearance of the new *Libertia* variety named 'NNGF2' showing colors as true as it is reasonably possible to obtain in colored reproductions of this type.

The drawing labeled

The drawing labeled

Figure 1:
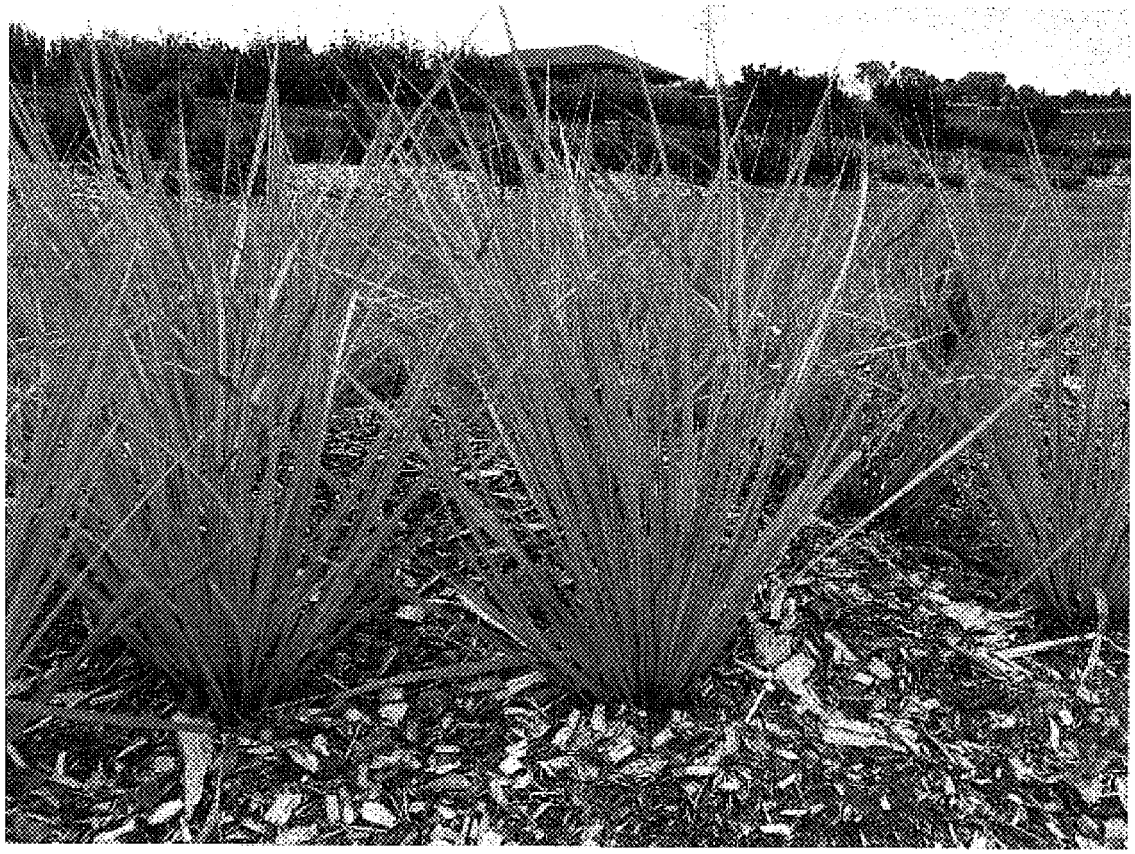
FIG. 1 depicts plants of 'NNGF2' from a side perspective illustrating habit. The plants shown are approximately 18 months old and have been grown out of doors in Auckland, New Zealand.
Figure 2:
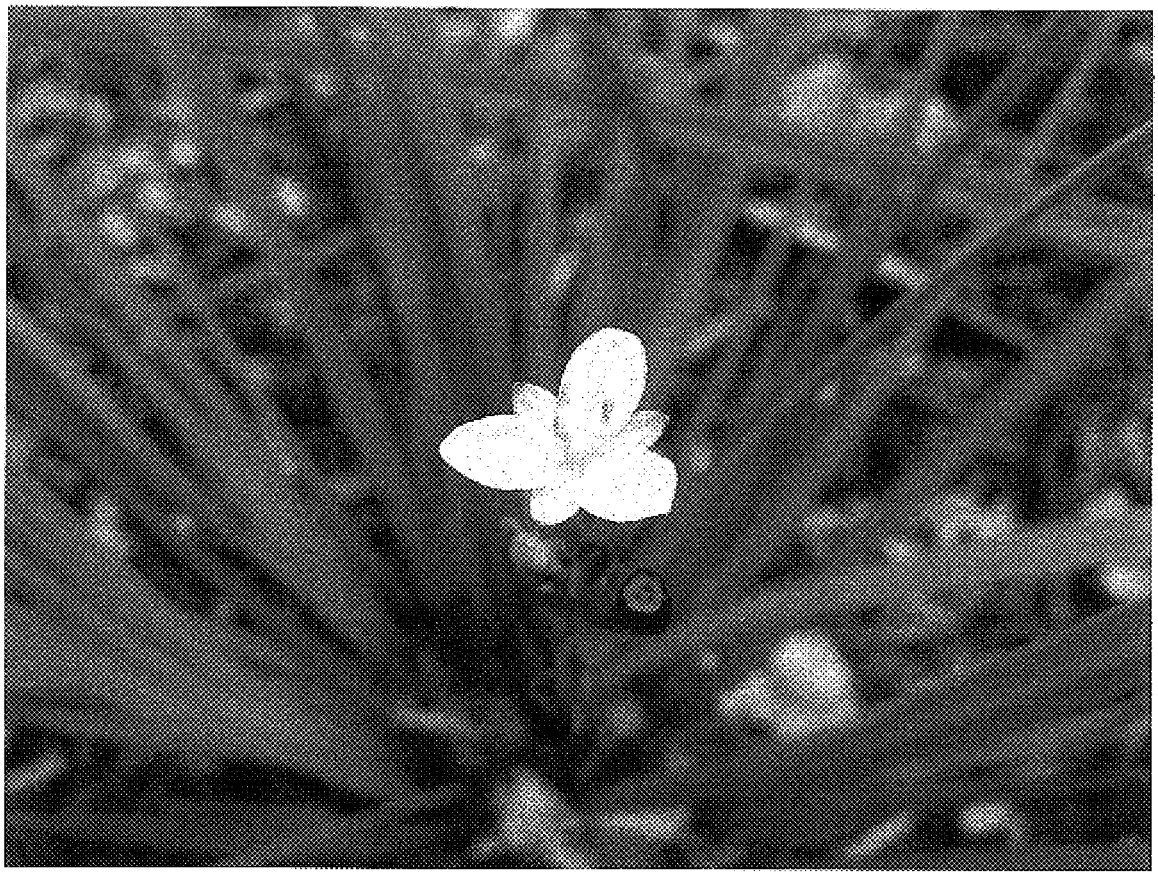
FIG. 2 is a close-up view of the flower. Color in the drawings may differ from color values cited in the detailed botanical description, which accurately describe the actual color of the new variety 'NNGF2'.

Drawings labeled FIG. 1 and FIG. 2 were made using conventional techniques and although flower and foliage color may appear different from actual color due to light reflectance, they are as accurate as possible by conventional photography.

BOTANICAL DESCRIPTION OF THE PLANT

The following is a detailed description of the new *Libertia* cultivar named 'NNGF2'. Data was collected and compiled in spring of 2006 in a cultivated area of Arroyo Grande, Calif. from 18 month old plants in 10 cm. container. Color determinations are in accordance with the 2001 Royal Horticultural Society Colour Chart of London, England except where general color terms of ordinary dictionary significance are used. The growing requirements are similar to the species.

Botanical classification: *Libertia ixioides* 'NNGF2'.
Family: Iridaceae.
Plant genus: *Libertia.*
Plant species: *ixioides.*
Plant denomination: 'NNGF2'.
Common name: New Zealand iris.
Plant use: Grown as an ornamental plant for container, border, deck, and patio.
Plant type: Perennial.
Parentage: The new cultivar *Libertia ixioides* 'NNGF2' was discovered as a naturally occurring seedling within a commercial crop of the following parents:
*Female parent plant.*—An individual *Libertia ixioides* 'Goldfinger'.
*Male parent plant.*—An individual *Libertia ixioides* 'Goldfinger'.
Plant vigor: Moderate.
Plant habit: Compact clumping fan-shaped habit.
Plant dimensions (10 cm. container plant): 19 cm. in height and 17 cm. in width.
Plant dimensions (first season): 0.3 m. in height and breadth.
Plant dimensions (at maturity): 0.6 m. in height and breadth.
Plant hardiness: Hardy to USDA Zone 7.
Plant propagation: Asexual propagation is achieved by the methods of tissue culture and division.
Plant root system: Fibrous.
Plant cultural requirements: Cultural requirements include adequate but not excess water, moist fertile soil, and full sun to partial shade.
Pest susceptibility or resistance: Older plants are susceptible to mealy bugs.
Disease susceptibility or resistance: None known to the inventor.
Time to produce liner: 8–12 weeks from tissue culture to a 5 cm. liner pot.
Plant crop time: 16–24 weeks from tissue culture to a finished 20 cm. container.
Seasonal interest: Flowers and berries.
Blooming season: Mid-spring to summer.
Foliage:
*Foliage type.*—Evergreen.
*Leaf quantity.*—Average of 19 leaves on a 10 cm. container plant.
*Leaf shape.*—Linear.
*Leaf texture.*—Soft and pliable.
*Leaf arrangement.*—Basal.
*Branching.*—Weeping to cascading.
*Leaf apex.*—Acute.
*Leaf base.*—Truncate.
*Leaf division:*—Simple.
*Leaf margin.*—Entire.
*Stipules.*—None observed.
*Leaf color (adaxial and abaxial surfaces).*—20A, 21A and 21 B, 146A.
*Leaf surface (adaxial and abaxial surfaces).*—Glabrous.
*Leaf venation pattern.*—Parallel veins.
*Leaf vein color (adaxial and abaxial surfaces).*—21B.
*Leaf length.*—Range of 5 cm. to 18 cm.
*Leaf width.*—Range of 0.40 cm. to 0.60 cm.
*Leaf fragrance.*—None observed.
Inflorescence:
*Blooming months.*—Late April to mid-July.
*Inflorescence type.*—Terminal panicle.
*Flower quantity.*—Average of 16 flowers per inflorescence.
*Persistent or self-cleaning.*—Self-cleaning.
*Flower aspect.*—Facing upward.
*Flower shape.*—Stellular.
*Flower depth.*—1 cm.
*Flower diameter.*—2 cm.
*Corolla tube depth.*—7 mm.
*Petals.*—3 in number.
*Petal dimensions.*—0.90 cm. in length and 0.60 cm. in width.
*Petals fused or unfused.*—Unfused.
*Petal shape.*—Rotund.
*Petal margin.*—Entire.
*Petal apex.*—Retuse.
*Petal base.*—Cordate.
*Petal surface.*—Glabrous.
*Petal color.*—155B.
*Calyx shape.*—Stellular.
*Calyx diameter.*—1 cm.
*Sepal number.*—3 in number.
*Sepals fused or unfused.*—Unfused.
*Sepal dimensions.*—4 mm. in length and 3 mm. in width.
*Sepal shape.*—Ovate.
*Sepal form.*—Petaloid.
*Sepal apex.*—Apiculate.
*Sepal base.*—Truncate.
*Sepal margin.*—Entire.
*Sepal surface.*—Glabrous.
*Sepal color.*—155B, 160A. 187C.
*Bud shape.*—Ovoid.
*Bud dimensions.*—2.25 mm. in diameter and 3 mm. in length.
*Bud color.*—155B, N144B, 160A 187C.
*Bud surface.*—Glabrous.
*Bud apex.*—Obtuse.
*Bud base.*—Truncate.
*Flower fragrance.*—None observed.
*Lastingness of flower.*—Range of 3–5 days on the plant.
*Flowering stem.*—Peduncle shape: Subterete. Peduncle surface: Glabrous. Peduncle color: 143A. Peduncle length: 20 cm. Peduncle width: 2 cm. Pedicel shape: Subterete. Pedicel surface: Glabrous. Pedicel color: 187C. Pedicel length: 1.25 cm. Pedicel width: 1 mm. Bract: Average of 4 per peduncle. Bract color: 143A. Bract dimensions: Average length 2.75 cm. and 0.60 cm. in width. Bract attachment: Sheathing. Bract shape: Ensiform and folded toward base. Bract margin: Entire. Bract apex: Epiculate. Bract base: Truncate. Bract surface: Glabrous. Bract internode length: 1.50 cm.

Reproductive organs:

*Stamens.*—Three.
*Stamen color.*—155B.
*Stamen length.*—1 cm.
*Anther color.*—160C.
*Anther dimensions.*—1.50 cm. in length and 2.50 mm. in width.
*Amount of pollen.*—Minimal.
*Pollen color.*—160C.
*Pistil length.*—0.75 cm.
*Pistil color.*—155B.
*Stigma shape.*—Forked.
*Stigma height and diameter.*—3 mm.
*Stigma color.*—155B (white).
*Ovary color.*—N144B.
*Ovary surface.*—Glabrous.
*Ovary appearance.*—Glossy.
*Ovary shape.*—Subterete.
*Ovary dimensions.*—0.20 cm. in diameter and 0.60 cm. in height.
*Ovary position.*—Inferior.

Fruit and seed:

*Dimensions of fruit.*—1.5 cm in length, 1 cm in width.
*Color of fruit.*—Green changing to golden with maturity.
*Texture of fruit.*—Capsule firm.
*Surface of fruit.*—Smooth oblong capsule which splits into three at the top to shed the seeds.
*Quantity of seeds per fruit.*—Seeds contained in three compartments within the capsule; approximately 20–30 seeds per capsule.
*Dimensions of seed.*—2 mm in length, 1.5 mm in diameter.
*Shape of seed.*—Rounded.
*Color of seed.*—Golden.
*Surface of seed.*—Smooth.

It is claimed:

1. A new and distinct variety of *Libertia* plant named 'NNGF2' as described and illustrated herein.

* * * * *